United States Patent

Hayakawa et al.

[11] Patent Number: 5,064,693
[45] Date of Patent: Nov. 12, 1991

[54] METHOD OF ADJUSTING A GAS SENSOR

[75] Inventors: Nobuhiro Hayakawa; Tetsusyo Yamada; Kazunori Yokota, all of Aichi, Japan

[73] Assignee: NGK Spark Plug Co., Ltd., Aichi, Japan

[21] Appl. No.: 420,694

[22] Filed: Oct. 11, 1989

Related U.S. Application Data

[63] Continuation of Ser. No. 235,716, Aug. 22, 1988, abandoned, which is a continuation of Ser. No. 945,993, Dec. 24, 1986, abandoned.

[30] Foreign Application Priority Data

Dec. 25, 1985 [JP] Japan .................. 60-294440

[51] Int. Cl.$^5$ ............................................ G01N 27/46
[52] U.S. Cl. ................................... 427/372.2; 422/88;
422/94; 422/95; 422/96; 427/97; 427/98;
427/402; 204/421; 204/424; 204/425; 204/428;
204/429
[58] Field of Search ................. 422/88, 94–98;
427/402, 403, 372.2; 204/428, 421–429

[56] References Cited

U.S. PATENT DOCUMENTS

| | | | |
|---|---|---|---|
| 3,092,799 | 6/1963 | Baker | 422/95 X |
| 3,564,474 | 2/1971 | Firth et al. | 422/97 X |
| 3,935,089 | 1/1976 | Towaga et al. | 204/195 S |
| 3,978,006 | 8/1976 | Topp et al. | 252/477 R |
| 4,072,467 | 2/1978 | Jones | 422/97 |
| 4,097,353 | 6/1978 | Kishida et al. | 204/195 S |
| 4,097,353 | 6/1978 | Kishida et al. | 204/195 S |
| 4,199,425 | 4/1980 | Sinkevitch | 204/195 S |

FOREIGN PATENT DOCUMENTS 1418280 12/1975 United Kingdom .
1538841 1/1979 United Kingdom .

Primary Examiner—David L. Lacey
Assistant Examiner—David Redding
Attorney, Agent, or Firm—Sughrue, Mion, Zinn, Macpeak & Seas

[57] ABSTRACT

A method of treating a porous body in a gas concentration sensor to regulate the gas diffusion. The porous body is impregnated with a impregnant containing a component that adheres to or binds with the pore surfaces. The component may be a metal salt, examples of which are $Al(NO_3)_3$, $CaCl_2$ and $H_2PtCl_2$. A colloidal solution may be used.

22 Claims, 2 Drawing Sheets

METHOD OF ADJUSTING A GAS SENSOR

This is a continuation of application Ser. No. 07/235,716, filed Aug. 22, 1988 now abandoned which is a continuation of application Ser. No. 06/945,993, filed Dec. 24, 1986.

BACKGROUND OF THE INVENTION

1. Field of the Invention

The present invention relates to a method of adjusting a gas sensor of the type, such as the "diffusion limited current" system, which measures the concentration of a gas of interest in an ambient atmosphere by employing the effect of limited gas diffusion into an analyzing compartment.

2. Background of the Invention

Techniques for achieving precise measurement of the concentration of gases in an ambient atmosphere are in great demand in areas of pollution control and for various industrial purposes. Two of the gas sensors that have been developed in order to attain this end are as follows. In one type, which is generally referred to as the "diffusion limited current" system, a solid electrolyte capable of conducting ions of a selected gaseous component is provided with a pair of electrodes to fabricate a pump element which is placed in contact with an analyzing compartment having a porous material that is capable of limiting gas diffusion. When a voltage is impressed on the pump element, a gaseous component of interest will be discharged out of the analyzing compartment and the concentration of that gas in the ambient atmosphere is measured in terms of the diffusion limited current flowing through the electrolyte. In the other type of gas sensor, either a concentration electrochemical cell having the same construction as the pump element or a gas sensing element is placed in contact with the analyzing compartment and the current flowing through the pump element is adjusted such that the electrochemical cell or gas sensing element will produce a constant output, and the concentration of a gas of interest in the ambient atmosphere is measured in terms of the adjusted current.

The gas concentration vs. output characteristics of the gas sensors described above are determined by the porosity of the porous body provided in the analyzing compartment, or its capability of limiting gas diffusion into that compartment. However, the porosity of the porous body is very subtle in nature and it has been impossible to achieve consistent production of gas sensors featuring uniform limitation of gas diffusion or postmanufacture adjustment of this parameter. Therefore, in order to achieve precise measurements of the concentration of a gas of interest, it has been necessary to adjust individual measuring circuits in accordance with the characteristics of the gas sensor employed.

SUMMARY OF THE INVENTION

The present invention has been accomplished in order to solve the aforementioned problems.

The invention provides a process of adjusting a gas sensor of the type which measures the concentration of a gas with a porous body being used as a gas diffusion limiting means. The process is characterized by treating the porous body with a liquid impregnant containing a component that adheres to or binds with said porous body.

DETAILED DESCRIPTION OF THE PREFERRED EMBODIMENTS

Two typical examples of gas sensors of the type which measure the concentration of a gas of interest in an ambient atmosphere by employing the gas diffusion limiting capability of a porous body (which lets in an ambient atmosphere in a limiting manner) have been described in the background section. Four embodiments of this type of sensor are shown in an unassembled state in FIG. 2(A) to (D).

Figure 2A:
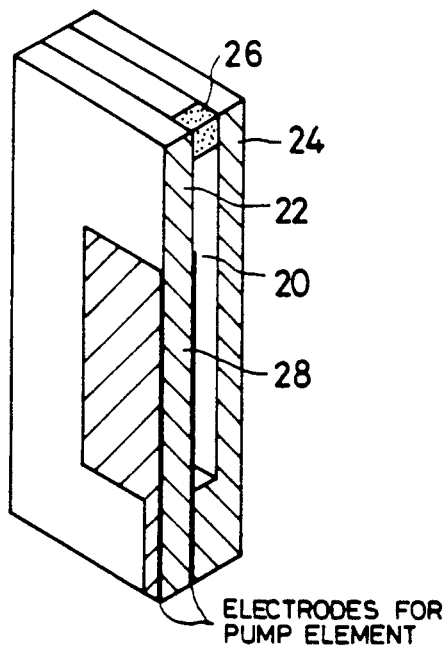
FIGS. 2(A) to (D) are perspective views showing in cross section four embodiments of a gas sensor employing a porous body as a gas diffusion limiting means.

In the embodiment shown in FIG. 2(A), a gas diffusing section in the form a small gap 20 is provided between a solid electrolyte 22 and a shield plate 24. A porous body 26 which lets in an ambient atmosphere is provided in an area that establishes communication between the gas diffusing section 20 and the ambient atmosphere. The gas sensor shown in FIG. 2(A) operates on the principle of "diffusion limited current" and determines the concentration of a gas of interest in terms of the limited current which is flowing through a pump element while it is pumping the gas of interest out of the gas diffusing section 20.

Figure 2B:
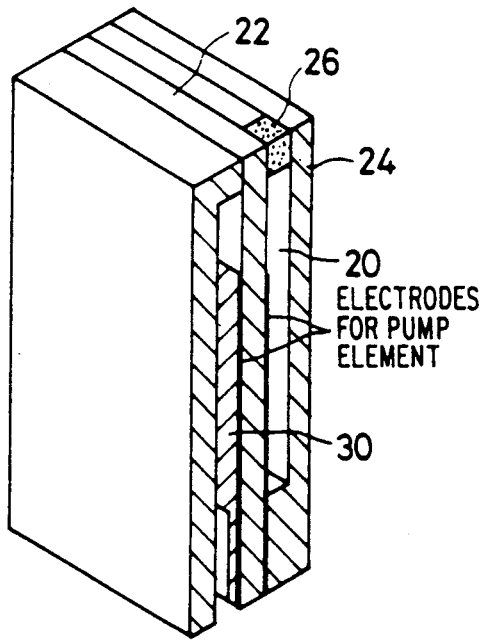

In the embodiment shown in FIG. 2(B), an atmosphere introducing channel 30 is provided on the side of the solid electrolyte 22, similar to that shown in FIG. 2(A), which is not exposed to the gas diffusing section 20. In this embodiment, the solid electrolyte 22 functions as a concentration electrochemical cell.

Figure 2C:
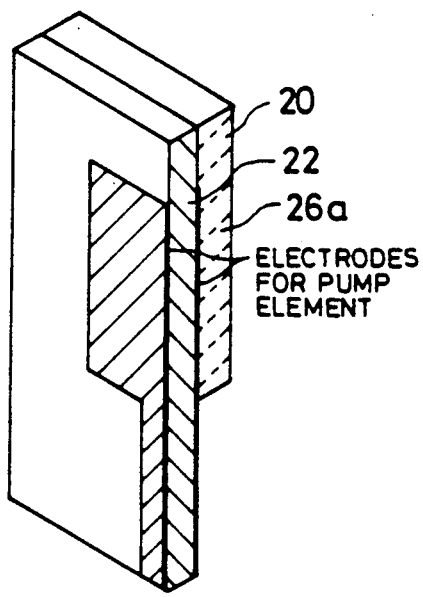

The gas diffusing section 20 shown in FIG. 2(A) may be filled with a porous body 26a as in the embodiment shown in FIG. 2(C). The porous body 26a has the capability of limiting gas diffusion and, therefore, the gas sensor shown in FIG. 2(C) operates on the principle of "diffusion limited current".

Figure 2D:
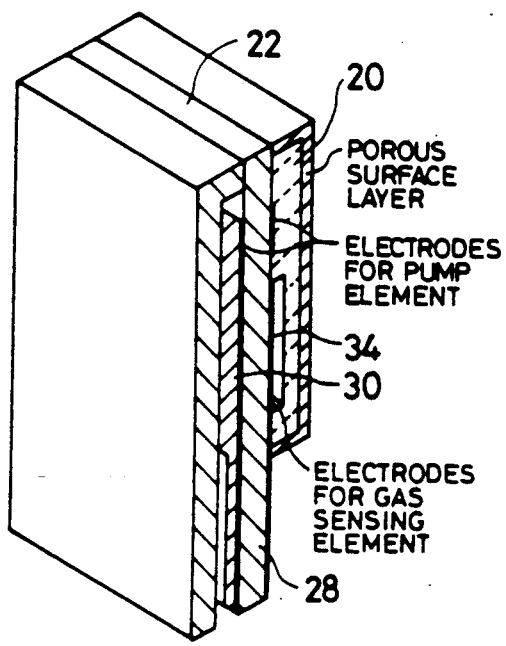

In the embodiment shown in FIG. 2(D), a gas sensing element 34 is provided within the gas diffusing section 20 and oxygen is supplied from the atmosphere with the pump element 28. It should be noted that the embodiments shown in FIGS. 2(A) to (D) are intended for illustrative purposes only and the concept of the present invention is applicable to every type of gas sensors that employ a porous body as a gas diffusion limiting means.

These sensors are capable of measuring the concentration of sodium gas if the solid electrolyte is made of beta-$Al_2O_3$, and of measuring oxygen gas if it is formed of a solid solution of a suitable compound such as stabilized $ZrO_2$, cerium dioxide, thorium dioxide or hafnium dioxide. Gas sensors of the type that employs both a pump element and a gas sensing element or a concentration electrochemical cell are also capable of measuring the concentrations of inflammable gases such as $H_2$, CO and $CH_4$ if an oxygen-ion conductive solid electrolyte is used. The gas sensing element may be formed of such materials as oxides of transition metals whose electrical conductivities will readily change in response to variations in the oxygen partial pressure of the ambient atmosphere.

The porous body used in the gas sensors described above may be made of $Al_2O_3$, mullite spinel or any other material whose porosity can be varied through adjustment of such factors as the grain size and the degree of refractoriness.

The liquid impregnant used in the present invention is required to contain a component that will adhere to or bind with the porous body 26. This component is preferably such that it turns highly heat-resistant after it has adhered to or bound with the porous body 26 since the gas sensor is typically exposed to high temperatures during service. It is also preferable that the component is in the form of either a colloid or solution that, can be readily impregnated in the porous body. The liquid impregnant may be a solution of a metal or silicon salt having high solubility, or a dispersion of a metal or silicon salt in a colloidal state, or a solution of an organometallic compound such as a metal or silicon alkoxide. Usable metal salts include nitrates, sulfates or chlorides of metal elements.

One preferable example is $Al(NO_3)_3$ which has a high solubility and produces stable $Al_2O_3$ after it has adhered to or bound with the porous body. Also preferable is $CaCl_2$ which has comparatively high solubility and turns into stable CaO after binding with the porous body. Platinic acid $[H_2(PtCl_4)]$ has the ability to afford catalytic properties to the porous body by being decomposed into Pt after it has adhered or joined to said porous body.

After being impregnated in the porous body in a gas sensor by dripping or any other appropriate means, the specified component in the liquid impregnant is permitted to adhere or bind to the porous body. This may be achieved by a decomposition or sintering reaction initiated by heating, or a chemical reaction which takes place during drying, or by a mechanical adhering or binding means.

In accordance with the present invention, the porous body used in a gas sensor is treated with the liquid impregnant specified above so that the porosity of the porous body will be adjusted to attain an optimum level of gas diffusion limitation as achieved by the porous body.

The pores in a porous body present pressure drag and limit the rate of gas diffusion. In other words, the ability of the porous body to limit gas diffusion is determined by its porosity. When the porous body is treated with the liquid impregnant described above, the component in the impregnant will adhere or bind to the walls of the pores present that so as to reduce their size (which is equivalent to saying that the porosity is decreased) and increase the pressure drag presented by the pores. As a result, the ability of the porous body to limit gas diffusion is increased. Therefore, by selecting the type and concentration of the liquid impregnant, the characteristics of any gas sensor can be properly adjusted to have desired values.

Figure 1:
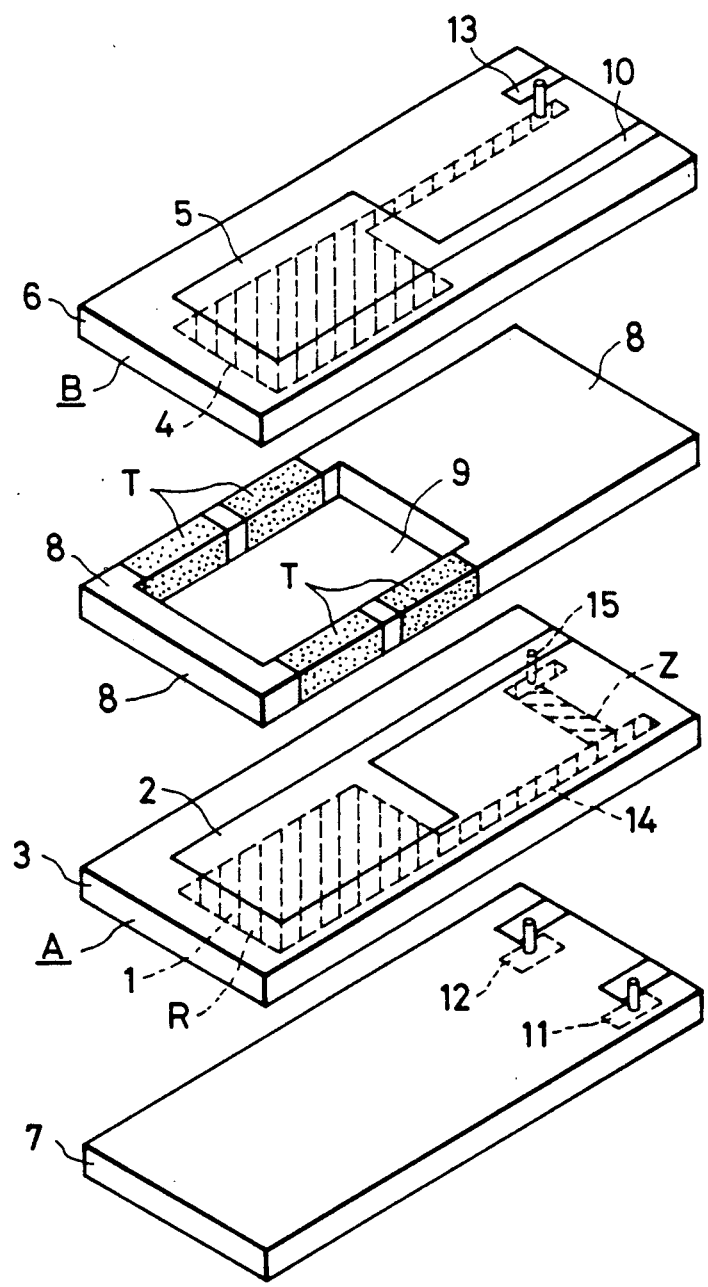
FIG. 1 is a perspective view showing, in an unassembled state, an air/fuel ratio sensor which may be treated by the method of the present invention in accordance with one embodiment.

An embodiment of the method of the present invention is hereunder described with reference to FIG. 1 which shows, in an unassembled state, an air/fuel ratio sensor to which the method of the present invention can be applied. As shown, the sensor comprises the following parts. A first element A is composed of a porous electrode 1, a porous electrode 2, and a solid electrolyte plate 3 between the two porous electrodes 1 and 2. A second element B is composed of an electrode 4, an electrode 5, and a solid electrolye plate 6 between the two electrodes 4 and 5. An internal reference oxygen source R is made in the form of the electrode 1 at the interface between the first element A and a shield plate 7. The electrode 1 is shown as being buried in the solid electrolyte plate 3.

A leakage resistance portion which is composed of a porous insulator Z and a lead 14 from the electrode 1. One end of the insulator Z contacts the lead 14 from the electrode 1 and the other end contacts a through-hole 15 connecting to the electrode 2. Finally, a gas compartment 9 is formed between the electrodes 2 and 4 on the first and second elements A and B, respectively, which are stacked together with a spacer 8 being inserted as a laminar intermediate member.

In the embodiment shown, the spacer 8 is cut out at four portions and filled with a porous body to provide gas diffusion limiting portions T.

The electrode 5 of the second element B is connected to a terminal 10, while the electrodes 1 and 2 of the first element A and electrode 4 of the second element B are connected to respective terminals 11, 12 and 13, through associated communicating holes.

The dimensions of the individual parts of the sensor are specified below. Each of the solid electrolyte plates, 3 and 6, measures 0.5 mm thick, 4 mm wide and 25 mm long. Each of the electrodes, 1, 2, 4 and 5, measures 2.4 mm by 7.2 mm. The spacer 8 measures 60 micrometers thick, 4 mm wide and 25 mm long. The gas compartment 9 formed in the spacer 8 measures 2.4 mm by 7.7 mm. The four gas diffusion limiting portions T are formed of a porous $Al_2O_3$ body and have a width of 1.7 mm. The shield plate 7 measures 0.5 mm thick, 4 mm wide and 25 mm long. The porous insulator is made of $Al_2O_3$ and measures 1 mm wide, 10 mm long and 30 micrometers thick.

The solid electrolyte plates 3 and 6 serving as the basis for the first and second elements A and B, respectively, are formed of a $Y_2O_3$ - $ZrO_2$ based solid electrolyte. Each of the electrodes 1, 2, 4 and 5 is formed of a porous body wherein platinum is doped with 10 wt % $Y_2O_3$ - $ZrO_2$. Both the shield plate 7 and the spacer 8 are made of zirconia.

A plurality of air/fuel ratio sensors having the construction shown above were fabricated and various liquid impregnants (see Table 1) were impregnated in the porous gas diffusion limiting portions T. After the impregnants were sintered, the resulting changes in the capability of the portions T to limit gas diffusion were examined. In order to determine the ability of a porous body to limit gas diffusion, the air/fuel sensors were operated to measure the concentration of oxygen in atmospheric air. As shown in FIG. 1, a constant current ($Is=25\mu A$) was allowed to flow through the first element A and a current Ip was permitted to flow through the second element B in such an amount that the electromotive force Vs developed in the first element A was 450 mV. During operation, each of the sensors was heated from both sides with a tabular heater so that the temperature of the sensing element was held constant to about 800° C. The measured value of Ip theoretically indicates the oxygen concentration of the atmospheric air (or the air/fuel ratio of an exhaust gas), but in the case under discussion, Ip directly indicates the ability of the porous gas diffusion limiting portions T to limit gas diffusion. The lower the value of Ip, the greater the ability of T to limit gas diffusion.

The method of determining the ability of a porous body to limit gas diffusion is by no means limited to the method described above and the generally employed method is to measure the value of Ip that flows when a predetermined voltage is applied to the pump element. The applied voltage is desirably sufficient to ensure that the oxygen partial pressure in the atmosphere around the electrode portion of the pump element that is subjected to diffusion limitation by the porous body is reduced to a very small value not exceeding $10^{-5}$ atmospheres.

The results of Icp measurements after treatment liquid impregnants are shown in Table 1.

TABLE 1

| Sample No. | Liquid impregnant | Icp before treatment (mA) | Icp after treatment (mA) | Rate of decrease* (%) |
|---|---|---|---|---|
| 1 | aqueous solution of $Al(NO_3)_3.9H_2O$ 400 g/liter | 28.0 | 21.4 | 23.6 |
| 2 | aqueous solution of $Al(NO_3)_3.9H_2O$ 400 g/liter | 24.0 | 17.2 | 28.3 |
| 3 | aqueous solution of $Al(NO_3)_3.9H_2O$ 400 g/liter | 17.4 | 13.0 | 25.3 |
| 4 | aqueous solution of $Al(NO_3)_3.9H_2O$ 400 g/liter | 18.3 | 13.7 | 25.1 |
| 5 | aqueous solution of $Al(NO_3)_3.9H_2O$ 200 g/liter | 28.1 | 24.4 | 13.2 |
| 6 | aqueous solution of $Al(NO_3)_3.9H_2O$ 200 g/liter | 18.5 | 15.9 | 14.1 |
| 7 | aqueous solution of $Al(NO_3)_3.9H_2O$ 200 g/liter | 18.1 | 15.3 | 15.5 |
| 8 | aqueous solution of $H_2PtCl_6.6H_2O$ 200 g/liter | 20.5 | 19.8 | 3.4 |
| 8a** | aqueous solution of $H_2PtCl_6.6H_2O$ 200 g/liter | 19.8 | 18.3 | 7.6 |
| 8b** | aqueous solution of $H_2PtCl_6.6H_2O$ 200 g/liter | 18.3 | 17.4 | 4.9 |
| 9 | aqueous solution of $H_2PtCl_6.6H_2O$ 200 g/liter | 22.8 | 21.9 | 3.9 |
| 9a** | aqueous solution of $H_2PtCl_6.6H_2O$ 200 g/liter | 21.9 | 20.6 | 5.9 |
| 9b** | aqueous solution of $H_2PtCl_6.6H_2O$ 200 g/liter | 20.6 | 19.5 | 5.3 |
| 10 | aqueous solution of $H_2PtCl_6.6H_2O$ 200 g/liter | 21.3 | 20.4 | 4.2 |
| 10a** | aqueous solution of $H_2PtCl_6.6H_2O$ 200 g/liter | 20.4 | 19.1 | 6.4 |
| 10b** | aqueous solution of $H_2PtCl_6.6H_2O$ 200 g/liter | 19.1 | 18.2 | 4.7 |
| 11 | aqueous solution of $CaCl_2$ 22.2 g/100 g | 18.9 | 14.7 | 22.2 |
| 12 | aqueous solution of $CaCl_2$ 22.2 g/100 g | 17.2 | 12.1 | 29.7 |
| 13 | aqueous solution of $CaCl_2$ 22.2 g/100 g | 17.0 | 12.0 | 29.4 |

*The rate of decrease was calculated by the following formula: 100-(Icp after treatment/Icp before treatment) × 100
**Samples No. 8a, 9a and 10a were the same as samples No. 8, 9 and 10, respectively, except that they were retreated with 200 g/liter of an aqueous solution of $H_2PtCl_6.6H_2O$. Samples No. 8b, 9b and 10b were the same as sample No. 8a, 9a and 10a, respectively, except that they were again retreated with 200 g/liter of an aqueous solution of $H_2PtCl_6.6H_2O$.

The above data shows that if two liquid impregnants are of the same type and concentration, the decreases in Icp are substantially constant irrespective of the value of Icp that flowed prior to treatment with the impregnants. Comparison of the data for sample Nos. 1 to 4 with those for sample Nos. 5 to 7 shows that changes in the concentration of an impregnant alone will cause corresponding decreases in Icp.

In accordance with the present invention, the porous body used in a gas sensor as a gas diffusion limiting means is treated with a liquid impregnant. This provides a simple method for adjusting the ability of the porous body to limit gas diffusion to thereby enable consistent production of gas sensors featuring uniform limitation on gas diffusion. A certain correlation exists between the type and concentration of a liquid impregnant and the change in the ability of the porous body to limit gas diffusion after it has been treated with said impregnant. Therefore, on the basis of a predetermined profile of this correlation, one will readily adjust the rate of gas diffusion limitation in a gas sensor to a desired value. For instance, it will be easy for those skilled in the art to fabricate a device that first measures the rate of gas diffusion limitation in a manufactured gas sensor and which then treat the sensor with several liquid impregnants that have known values of adjustment of the rate of gas diffusion limitation.

We claim:

1. In a process for producing a gas sensor that comprises a pump element having a pair of electrodes formed on a solid electrolyte that conducts ions of a gaseous component of interest and a porous material that is capable of limiting gas diffusion and which is interposed between one of said electrodes of said pump element and a gas to be analyzed that contains said gaseous component of interest, an electric current being allowed to flow through said pump element so as to change a concentration of said gaseous component of interest, said gaseous component of interest being permitted to diffuse through said porous material, and said concentration of said gaseous component of interest in said gas to be analyzed being related to a value of said applied current that corresponds to an amount of said gas diffusion so as to measure said concentration of said gaseous component of interest, the improvement wherein said process comprises the steps of:

providing an electrolytic liquid impregnant containing a predetermined concentration of a component that adheres to or binds with said porous material;

applying an electric current to the pump element so as to determine dan ability of said porous material in said gas sensor to limit gas diffusion;

impregnating or dripping said liquid impregnant in said porous material in an amount dependent upon said determination of said ability of said porous material to limit gas diffusion so as to adjust the porosity of the porous body to attain an optimum level of gas diffusion limitation; and heating or drying said treated porous material so that said component will be adhered or bound to said porous material.

2. A method as recited in claim 1, wherein said liquid impregnant is a solution of a metal salt.

3. A method as recited in claim 2, wherein said metal salt is composed of $Al((NO_3)_3$.

4. A method as recited in claim 2, wherein said metal salt is composed of $CaCl_2$.

5. A method as recited in claim 2, wherein said metal salt is composed of $H_2PtCl_6$.

6. A process as recited in claim 1 wherein said gaseous component of interest is oxygen gas.

7. A process as recited in claim 1 wherein said liquid impregnant is a solution of an organometallic compound.

8. A process as recited in claim 1 wherein said liquid impregnant is a solution of silicon salt.

9. The process as recited in claim 1, wherein said liquid impregnant is $Al(NO_3)_3$.

10. The process as recited in claim 1, wherein said liquid impregnant is $H_2PtCl_2$.

11. In a process for producing a gas sensor that comprises a pump element having a pair of electrodes formed on a solid electrolyte that conducts ions of a gaseous component of interest and a porous material that is capable of limiting gas diffusion and which is interposed between one of said electrodes of said pump element and a gas to be analyzed that contains said gaseous component of interest, an electric current being allowed to flow through said pump element so as to change a concentration of said gaseous component of interest, said gaseous component of interest being permitted to diffuse through said porous material, and said concentration of said gaseous component of interest in said gas to be analyzed being related to a value of said applied current that corresponds to an amount of said gas diffusion so as to measure said concentration of said gaseous component of interest, the improvement wherein said process comprises the steps of:

measuring a gas diffusion resistance using said pair of electrodes of said sensor and said electric current flowing through said pump element; and modifying the porosity of said porous material by impregnating an electrolytic liquid therein to adjust said porosity so as to achieve a predetermined gas diffusion resistance in accordance with an initial determination of said gas diffusion resistance.

12. The process as recited in claim 11 wherein said gaseous component of interest is oxygen gas.

13. The process as recited in claim 11 wherein said liquid impregnant is a solution of organometallic compound.

14. The process as recited in claim 11 wherein said liquid impregnant is a solution of silicate salt.

15. The process as recited in claim 11, wherein said liquid impregnant is $Al(NO_3)_3$.

16. The process as recited in claim 11, wherein said liquid impregnant is $H_2PtCl_2$.

17. In a process for producing a gas sensor that comprises a pump element for conducting ions of a gaseous component of interest, a porous body for limiting gas diffusion, and a sensor cell for determining the ability of said porous body to limit diffusion of said gaseous component of interest, the improvement wherein said process comprises the steps of:

heating said gas sensor to a predetermined temperature;

applying a constant current through said sensor cell;

adjusting the current through said pump element to obtain a predetermined voltage across said sensor cell;

measuring the current through said pump element required to obtain the predetermined voltage across said sensor cell; and impregnating said porous material with an electrolytic liquid impregnant, comprising a component which adheres to or binds with said porous material, in an amount determined in accordance with the measured current through said pump element to adjust a porosity of said porous material so as to obtain a desired gas diffusion resistance.

18. The process as recited in claim 17 wherein said gaseous component of interest is oxygen gas.

19. The process as recited in claim 17 wherein said liquid impregnant is a solution of organometallic compound.

20. The process as recited in claim 19, wherein said liquid impregnant is a solution of silicate salt.

21. The process as recited in claim 17, wherein said liquid impregnant is $Al(NO_3)_3$.

22. The process as recited in claim 17, wherein said liquid impregnant is $H_2PtCl_2$.

* * * * *